(12) United States Patent
Li et al.

(10) Patent No.: US 9,580,403 B2
(45) Date of Patent: Feb. 28, 2017

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Xiaoyong Li, Midland, MI (US); Qiang Yang, Zionsville, IN (US); Gary Roth, Midland, MI (US); Beth Lorsbach, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/988,773

(22) Filed: Jan. 6, 2016

(65) Prior Publication Data

US 2016/0152593 A1 Jun. 2, 2016

Related U.S. Application Data

(63) Continuation of application No. 14/666,814, filed on Mar. 24, 2015, now Pat. No. 9,255,081, which is a continuation of application No. 14/517,349, filed on Oct. 17, 2014, now Pat. No. 9,029,555.

(60) Provisional application No. 62/031,533, filed on Jul. 31, 2014.

(51) Int. Cl.
*C07D 401/04* (2006.01)

(52) U.S. Cl.
CPC .................. *C07D 401/04* (2013.01)

(58) Field of Classification Search
CPC .................................................. C07D 401/04
USPC ...................................................... 546/275.4
See application file for complete search history.

(56) References Cited

U.S. PATENT DOCUMENTS

| | | | |
|---|---|---|---|
| 3,597,341 A | 8/1971 | Oswald | |
| 4,080,457 A | 3/1978 | Harrison et al. | |
| 4,260,765 A | 4/1981 | Harrison et al. | |
| 4,407,803 A | 10/1983 | Haviv et al. | |
| 4,536,506 A | 8/1985 | Marcoux et al. | |
| 4,824,953 A | 4/1989 | Bronn | |
| 5,220,028 A | 6/1993 | Iwasawa et al. | |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |
| 5,817,677 A | 10/1998 | Linz et al. | |
| 5,854,264 A | 12/1998 | Anthony et al. | |
| 5,854,265 A | 12/1998 | Anthony et al. | |
| 5,869,681 A | 2/1999 | Muller et al. | |
| 6,040,331 A | 3/2000 | Yamamoto et al. | |
| 6,218,418 B1 | 4/2001 | Pevarello et al. | |
| 6,506,747 B1 | 1/2003 | Betageri et al. | |
| 6,548,525 B2 | 4/2003 | Galemmo, Jr. et al. | |
| 6,720,427 B2 | 4/2004 | Sanner et al. | |
| 6,878,196 B2 | 4/2005 | Harada et al. | |
| 6,916,927 B2 | 7/2005 | Bunnage et al. | |
| 6,965,032 B2 | 11/2005 | Freudenberger et al. | |
| 7,192,906 B2 | 3/2007 | Hirohara et al. | |
| 7,196,104 B2 | 3/2007 | Askew, Jr. et al. | |
| 7,319,108 B2 | 1/2008 | Schwink et al. | |
| 7,774,978 B2 | 8/2010 | Ding et al. | |
| 7,803,832 B2 | 9/2010 | Critcher et al. | |
| 7,910,606 B2 | 3/2011 | Nazare et al. | |
| 7,923,573 B2 | 4/2011 | Tamaki et al. | |
| 8,163,756 B2 | 4/2012 | Flynn et al. | |
| 8,222,280 B2 | 7/2012 | Liu et al. | |
| 8,901,153 B2 | 12/2014 | Buysse et al. | |
| 9,024,031 B1 | 5/2015 | Yang et al. | |
| 9,029,554 B1 | 5/2015 | Yang et al. | |
| 9,029,555 B1* | 5/2015 | Li ........................ | C07D 401/04 546/275.4 |
| 9,029,556 B1 | 5/2015 | Yang et al. | |
| 9,044,017 B2 | 6/2015 | Yang et al. | |
| 9,085,552 B1 | 7/2015 | Li et al. | |
| 9,085,564 B2 | 7/2015 | Yang et al. | |
| 9,102,654 B2 | 8/2015 | Yang et al. | |
| 9,102,655 B2 | 8/2015 | Yang et al. | |
| 9,102,656 B2 | 8/2015 | Yang et al. | |
| 9,108,932 B2 | 8/2015 | Ross et al. | |
| 9,108,946 B2 | 8/2015 | Yang et al. | |
| 9,115,115 B1 | 8/2015 | Yang et al. | |
| 9,126,974 B2 | 9/2015 | Yang et al. | |
| 9,156,813 B1 | 10/2015 | Li et al. | |
| 9,174,962 B2 | 11/2015 | Yang et al. | |
| 9,199,942 B2 | 12/2015 | Yang et al. | |
| 9,199,964 B1 | 12/2015 | Yang et al. | |
| 2002/0013326 A1 | 1/2002 | Tiebes et al. | |
| 2003/0153464 A1 | 8/2003 | Nakamura et al. | |
| 2003/0213405 A1 | 11/2003 | Harada et al. | |
| 2004/0043904 A1 | 3/2004 | Yamaguchi et al. | |
| 2004/0082629 A1 | 4/2004 | Iwataki et al. | |
| 2005/0038059 A1 | 2/2005 | Mueller et al. | |

(Continued)

FOREIGN PATENT DOCUMENTS

| | | |
|---|---|---|
| EP | 0097323 | 1/1984 |
| EP | 0190457 | 8/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.

(Continued)

*Primary Examiner* — Patricia L Morris

(74) *Attorney, Agent, or Firm* — Carl D. Corvin; Barnes & Thornburg LLP

(57) ABSTRACT

3-(3-Chloro-1H-pyrazol-1-yl)pyridine is prepared by cyclizing 3-hydrazinopyridine-dihydrochloride with commercially available 3-ethoxyacrylonitrile to provide 3-(3-amino-1H-pyrazol-1-yl)pyridine, and by converting the amino group to a chloro group by a Sandmeyer reaction.

9 Claims, No Drawings

(56) References Cited

U.S. PATENT DOCUMENTS

| | | |
|---|---|---|
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2011/045224 | 10/2009 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011-134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2010/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |

OTHER PUBLICATIONS

Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.

Bradbury et al., "Enzyme-catalysed peptide amidation," Eur. J. Biochem. 1987, vol. 169, pp. 579-584.

International Search Report and Written Opinion for PCT/US2014/061005 mailed Dec. 16, 2014.

International Search Report and Written Opinion for PCT/US2014/061006 mailed Dec. 8, 2014.

International Search Report and Written Opinion for PCT/US2014/061007 mailed Dec. 31, 2014.

(56) References Cited

OTHER PUBLICATIONS

International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Search Report and Written Opinion for PCT/US2011/058578 mailed Apr. 5, 2012.

\* cited by examiner

PROCESS FOR THE PREPARATION OF 3-(3-CHLORO-1H-PYRAZOL-1-YL)PYRIDINE

CROSS REFERENCE TO RELATED APPLICATIONS

This application is a continuation of U.S. application Ser. No. 14/666,814 filed on Mar. 24, 2015, which is a continuation of U.S. application Ser. No. 14/517,349 filed on Oct. 17, 2014, which claims the benefit of U.S. Provisional Patent Application Ser. No. 62/031,533, filed Jul. 31, 2014, the entire disclosures of which are hereby expressly incorporated by reference in this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yl)pyridine (5b) by the direct coupling of 3-bromopyridine with 3-chloropyrazole. The 3-chloropyrazole was prepared by a) treating 1H-pyrazole with 2-dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine that avoids these problems.

SUMMARY

The present invention provides such an alternative by cyclizing 3-hydrazinopyridine-•dihydrochloride with commercially available 3-ethoxyacrylonitrile to provide 3-(3-amino-1H-pyrazol-1-yl)pyridine (8a), and by converting the amino group to a chloro group by a Sandmeyer reaction. Thus, the present invention concerns a process for preparing 3-(3-chloro-1H-pyrazol-1-yl)pyridine (5b),

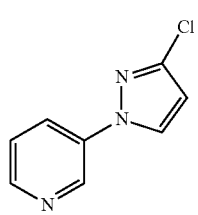

which comprises
a) treating 3-hydrazinopyridine•dihydrochloride

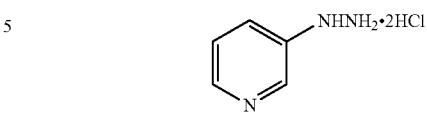

with 3-ethoxyacrylonitrile

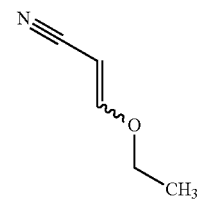

in a $(C_1-C_4)$ aliphatic alcohol at a temperature of about 25° C. to about 100° C. in the presence of an alkali metal $(C_1-C_4)$ alkoxide to provide 3-(3-amino-1H-pyrazol-1-yl)pyridine (8a)

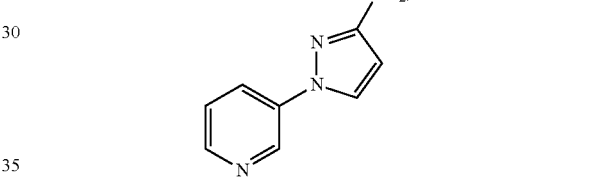

b) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

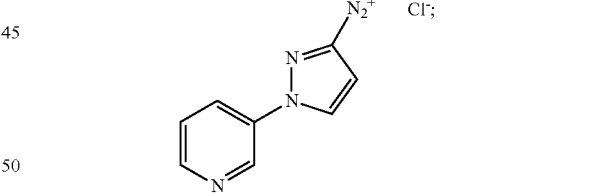

and
c) treating the diazonium salt (8b) with copper chloride at a temperature of about 0° C. to about 25° C.

DETAILED DESCRIPTION

The present invention provides an improved process for preparing 3-(3-chloro-1H-pyrazol-1-yl)pyridine (5b) by cyclizing 3-hydrazinopyridine•dihydrochloride with commercially available 3-ethoxyacrylonitrile to provide 3-(3-amino-1H-pyrazol-1-yl)pyridine (8a), and by converting the amino group to a chloro group by a Sandmeyer reaction.

In the first step, 3-hydrazinopyridine•dihydrochloride is treated with 3-ethoxyacrylonitrile in a $(C_1-C_4)$ aliphatic alcohol at a temperature of about 25° C. to about 100° C. in the presence of an alkali metal $(C_1-C_4)$ alkoxide to provide 3-(3-amino-1H-pyrazol-1-yl)pyridine (8a). While stoichiometric amounts of 3-hydrazinopyridine•dihydrochloride and 3-ethoxyacrylonitrile are required, it is often convenient to use about a 1.5 fold to about a 2 fold excess of 3-ethoxyacrylonitrile. The cyclization is run in the presence of an alkali metal ($C_1$-$C_4$) alkoxide base. It is often convenient to use about a 2 to about a 5 fold excess of base. The cyclization is performed in a ($C_1$-$C_4$) aliphatic alcohol. It is most convenient that the alkoxide base and the alcohol solvent be the same, for example, sodium ethoxide in ethanol. It is appreciated that methoxyacrylonitrile and propoxyacrylonitrile would be suitable for effecting this cyclization.

In a typical reaction, 3-hydrazinopyridine•dihydrochloride and an anhydrous alcohol are introduced into a reaction vessel and the alkoxide base is gradually added. The mixture is stirred and the 3-ethoxyacrylonitrile is added. The mixture is stirred at about 80° C. until most of the 3-hydrazinopyridine has reacted. The mixture is allowed to cool and the excess base is neutralized with acid. The crude 3-(3-amino-1H-pyrazol-1-yl)pyridine (8a) is conveniently isolated and purified by standard techniques.

The 3-(3-amino-1H-pyrazol-1-yl)pyridine (8a) is then converted to the desired 3-(3-chloro-1H-pyrazol-1-yl)pyridine (5b) by treatment in aqueous hydrochloric acid with sodium nitrite at a temperature of about 0° C. to about 25° C. to provide a diazonium salt followed by treatment of the diazonium salt with copper chloride at a temperature of about 0° C. to about 25° C. While stoichiometric amounts of reagents are required, it is often convenient to use an excess of reagents with respect to the 3-(3-amino-1H-pyrazol-1-yl)pyridine (8a). Thus, aqueous hydrochloric acid is used in large excess as the reaction medium. Sodium nitrite is used in about a 1.3 fold to about a 2 fold excess. Copper chloride is used in about 5 mole percent to about 60 mole percent excess, preferably from about 15 mole percent to about 30 mole percent excess. The copper chloride may be either copper(I) chloride or copper(II) chloride. To suppress foaming during the reaction a water-immiscible organic solvent such as toluene or chloroform can be added during the treatment of the diazonium salt with copper chloride.

In a typical reaction, a mixture of 3-(3-amino-1H-pyrazol-1-yl)pyridine (8a) and aqueous hydrochloric acid are mixed and cooled to about 0° C. An aqueous solution of sodium nitrite is slowly added maintaining the temperature below about 5° C. The suspension is stirred at about 0° C. for about 2 hours. In a separate vessel, a mixture of copper(I) chloride and toluene is cooled to about 0° C. and the chilled suspension of diazonium salt is added at a rate maintaining the temperature below about 5° C. The mixture is allowed to warm to about ambient temperature. After completion of the reaction, the mixture is treated with aqueous sodium hydroxide to adjust the pH to about 8 to about 10. The resulting solution is extracted with a water-immiscible organic solvent. After removal of the solvent, the 3-(3-chloro-1H-pyrazol-1-yl)pyridine (5b) can be used directly in the next step or further purified by standard techniques such as flash column chromatography or crystallization.

The following examples are presented to illustrate the invention.

EXAMPLES

1. Preparation of 3-(3-amino-1H-pyrazol-1-yl)pyridine (8a)

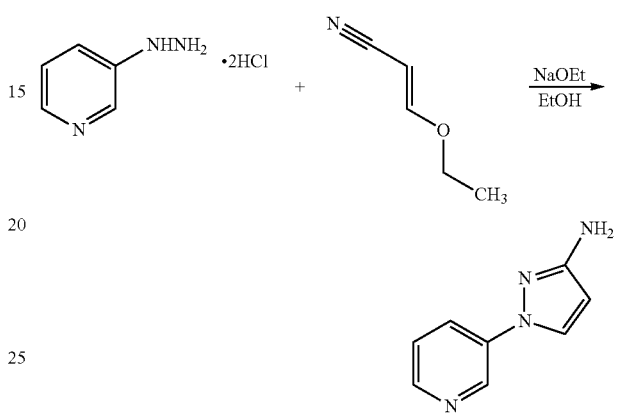

To a three-neck round bottomed flask (50 mL) equipped with a reflux condenser was introduced 3-hydrazinopyridine•dihydrochloride (1.82 g, 10.0 mmol) and anhydrous ethanol (10.0 mL). Sodium ethoxide (21 wt % in EtOH, 11.8 mL, 31.5 mmol) was added over 5 minutes and the internal temperature increased from 23° C. to 30° C. The resultant light brown slurry turned light pink after stirring for 10 minutes. 3-Ethoxyacrylonitrile (2.06 mL, 20.0 mmol) was added over 5 minutes and the internal temperature remained at 30° C. The yellow mixture was stirred at 78° C. under nitrogen for 5 hours and was then cooled to 15° C. Hydrochloric acid (4 M in 1,4-dioxane, 2.90 mL) was added slowly to quench any excess base forming a light brown suspension. The mixture was concentrated under reduced pressure to afford a brown solid. The solid was partitioned in water (30 mL) and ethyl acetate (50 mL). The insoluble light brown solid was collected by filtration to afford the first portion of product (0.340 g, >95% pure by $^1$H NMR). The aqueous layer was extracted with ethyl acetate (3×50 mL). The combined organic extracts were concentrated to afford dark brown wet solid. The mixture was suspended in ethyl acetate (10 mL), filtered, and washed with heptane (20 mL) to afford the second portion of product as a brown solid (1.00 g, >95% pure by $^1$H NMR). The title compound was obtained as a brown solid (1.34 g, 84%): $^1$H NMR (400 MHz, DMSO-$d_6$) δ 8.93 (d, J=2.4 Hz, 1H), 8.33 (dd, J=4.8, 1.2 Hz, 1H), 8.23 (d, J=2.4 Hz, 1H), 8.01 (ddd, J=8.4, 2.8, 1.2 Hz, 1H), 7.42 (dd, J=8.4, 4.8 Hz, 1H), 5.80 (d, J=2.4 Hz, 1H), 5.19 (bs, 2H, —$NH_2$); $^{13}$C NMR (100 MHz, DMSO-$d_6$) δ 157.7, 144.7, 138.0, 136.2, 128.3, 123.9, 123.2, 97.1; EIMS m/z 160 (Mr); HPLC (Zorbax SB-C8 column, P/N: 863954-306; mobile phase: A=water (0.1% formic acid), B=acetonitrile (0.01% formic acid); Gradient from 5 to 100% acetonitrile over 15 minutes; flow: 1.0 mL/minute): $t_R$=1.95 minutes.

2. Preparation of 3-(3-chloro-1H-pyrazol-1-yl)pyridine (5b)

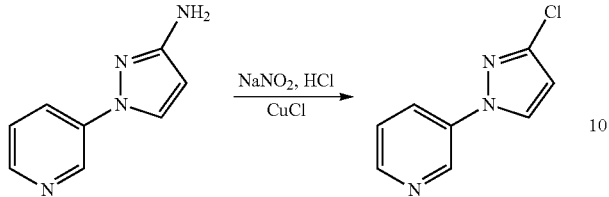

To a three-neck round bottomed flask (25 mL) was introduced 3-amino-1-(3-pyridyl)-pyrazole (0.480 g, 3.00 mmol) and concentrated hydrochloric acid (4.6 mL). The vigorously stirred mixture was cooled to −5° C. using a sodium chloride ice-bath. Sodium nitrite (0.269 g, 3.90 mmol) in water (1.3 mL) was added dropwise over 40 minutes while maintaining the temperature at −5° C. The resultant dark orange mixture was stirred for 1 hour between −5° C. and −0° C. and then added dropwise into a suspension of copper(I) chloride (0.475 g, 4.80 mmol) in chloroform (4.8 mL) at 25° C. over 15 minutes. The dark green slurry was stirred at room temperature for 1 hour. Water (10 mL) and chloroform (10 mL) was added to the mixture leading to a dark green solution. The acidic aqueous solution was neutralized by sodium hydroxide (50% in water) to pH 8 and extracted with chloroform (2×10 mL) and ethyl acetate (3×20 mL). The combined organic extracts were dried over anhydrous sodium sulfate and concentrated under reduced pressure to afford crude product as a yellow solid (0.476 g). LC assay using di-n-propyl phthalate as internal standard indicated 73.7% purity (0.351 g, 65%): $^1$H NMR (400 MHz, CDCl$_3$) δ 8.94 (d, J=2.8 Hz, 1H), 8.57 (dd, J=4.8, 1.2 Hz, 1H), 8.03 (ddd, J=8.4, 2.8, 1.6 Hz, 1H), 7.90 (d, J=2.4 Hz, 1H), 7.41 (ddd, J=8.4, 4.8, 0.8 Hz, 1H), 6.45 (d, J=2.4 Hz, 1H); EIMS m/z 179 ([1\4]$^+$); HPLC (Zorbax SB-C8 column, P/N: 863954-306; mobile phase: A=water (0.1% formic acid), B=acetonitrile (0.01% formic acid); Gradient from 5 to 100% acetonitrile over 15 minutes; flow: 1.0 mL/minute): $t_R$=6.28 minutes.

What is claimed is:

1. A process for preparing 3-(3-amino-1H-pyrazol-1-yl)pyridine (8a)

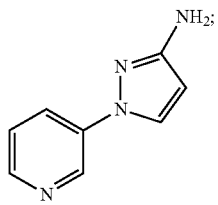

comprising
treating 3-hydrazinopyridine·dihydrochloride

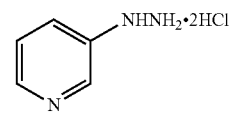

with an alkoxyacrylonitrile in a (C$_1$-C$_4$) aliphatic alcohol at a temperature of about 25° C. to about 100° C. in the presence of an alkali metal (C$_1$-C$_4$) alkoxide.

2. The process of claim 1, wherein the alkoxyacrylonitrile is in about a 1.5-fold to about a 2-fold excess.

3. The process of claim 1, wherein the alkoxyacrylonitrile is methoxyacrylonitrile, ethoxyacrylonitrile or propoxyacrylonitrile.

4. The process of claim 3, wherein the alkoxyacrylonitrile is methoxyacrylonitrile.

5. The process of claim 3, wherein the alkoxyacrylonitrile is ethoxyacrylonitrile.

6. The process of claim 3, wherein the alkoxyacrylonitrile is propoxyacrylonitrile.

7. The process of claim 1, wherein the alkali metal (C$_1$-C$_4$) alkoxide is sodium ethoxide, and the (C$_1$-C$_4$) aliphatic alcohol is ethanol.

8. The process of claim 1, wherein the alkali metal (C$_1$-C$_4$) alkoxide is used in about a 2 to about a 5 fold excess.

9. The process of claim 1, wherein the alkali metal (C$_1$-C$_4$) alkoxide is neutralized with an acid.

* * * * *